United States Patent

Lee et al.

[11] Patent Number: 5,104,513
[45] Date of Patent: Apr. 14, 1992

[54] GAS SENSOR

[75] Inventors: Tony C. Lee, Syracuse; Thomas A. Schmitkons, Baldwinsville, both of N.Y.

[73] Assignee: Leybold Inficon Inc., E. Syracuse, N.Y.

[21] Appl. No.: 600,481

[22] Filed: Oct. 18, 1990

[51] Int. Cl.⁵ .......................................... G01N 27/407
[52] U.S. Cl. .................... 204/425; 73/31.05; 204/426; 204/431
[58] Field of Search ............... 204/424, 425, 431, 426; 73/31.05; 422/98

[56] References Cited

U.S. PATENT DOCUMENTS

| | | | |
|---|---|---|---|
| 3,751,968 | 8/1973 | Loh et al. | 73/31.05 |
| 3,979,625 | 9/1976 | Roberts | 313/230 |
| 3,991,360 | 11/1976 | Orth et al. | 324/468 |
| 4,129,418 | 12/1978 | Davis | 422/98 |
| 4,171,341 | 10/1979 | Morgan | 422/98 |
| 4,822,465 | 4/1989 | Jones et al. | 204/192.1 |
| 4,947,125 | 8/1990 | De Pous | 324/459 |

Primary Examiner—John Niebling
Assistant Examiner—William T. Leader
Attorney, Agent, or Firm—Wall and Roehrig

[57] ABSTRACT

A sensor for selectively sensing the presence of halogenated gases, particularly HFC's, within an atmosphere. The apparatus includes a ceramic element containing either a mixture of alkali metal silicates and aluminum oxide or aluminosilicate which react with ions of the halogenated gas when the two are brought together forming a depletion layer on and within the ceramic. A preferred ceramic composition is a mixture of potassium slicate and either one of silicon dioxide or aluminum oxide. The sensor is formed with two electrodes on opposite sides of the ceramic having terminals connected into a circuit for detecting a potential difference across the depletion layer. Means are provided for detecting the potential differences and for producing a discernable signal in response thereto.

12 Claims, 1 Drawing Sheet 5,104,513

GAS SENSOR

BACKGROUND OF THE INVENTION

This invention relates to an improved solid state sensing device for selectively detecting the presence of gases within an atmosphere, particularly refrigerant gases such as hydrofluorocarbons (HFC's) and sulphur hexafluoride.

There are many instances where it is necessary to detect the presence of specific gases or vapors in an atmosphere. The gas or vapor may be harmful to human health and thus it may be desirable to monitor a work environment to insure that the concentration of the gas or vapor does not exceed some threshold level. Or, it may be desirable to test pressurized equipment for leaks which could indicate a malfunction. Particular types of gases or vapors which it is desirable to be able to detect are halogen containing gases such as those used as refrigerants and fire extinguishants. For proper operation, leaks from refrigeration, air conditioning, and fire extinguishing equipment must be eliminated or kept to a minimum. Thus, it is necessary to test both components and final assemblies for leaks.

The widely used chlorofluorocarbon (CFC) refrigerants R-12 and R-11 and the fire extinguishants HALON 1301 and HALON 1211 are among the group of chlorinated and/or brominated compounds being phased out or severely restricted by international agreement due to their potential for destroying ozone in the upper atmosphere. The substitutes for these materials in most applications are either hydrofluorocarbons (HFC's) which have no ozone depletion potential or hydrochlorofluorocarbons (HCFC's) which have a significantly reduced ozone depletion potential. For example, the HFC, R-134a, is replacing R-12 in refrigeration and air conditioning applications where stringent leak testing is required to insure adequate performance of the equipment. Suitable means for detecting leaks is a critical factor in the conversion of this industry to non-ozone depleting chemicals. Although present state of the art gas sensors are quite effective for detecting chlorinated and brominated gases (CFC's, HCFC's, and HALONS), they are not adequate for detecting HFC's.

The prior art of sensors for detecting gases or vapors in an atmosphere has utilized a number of different detection principles. These include 1) measuring changes in the rate of heat loss from a circuit component resulting from changes in thermal conductivity of the atmosphere being sampled 2) electron capture methods which measure ions formed by the gas of interest when it is exposed to low energy electrons 3) positive ion emission methods in which the gas of interest facilitates emission of positive ions from a metal surface in the presence of a strong electric field, and 4) depletion layer methods in which the gas of interest alters the concentration of charge carrying species in a surface depletion layer and thus changes the internal resistance of the sensor.

These prior art sensors all have problems in regard to detection of HFC's. Thermal conductivity detectors are not specific to a given gas and thus are likely to give false responses. They also do not have as high a sensitivity as other types of detectors. Electron capture detectors use a radioactive source which requires special handling and in most cases must be licensed by governmental authorities. Prior art positive ion emission and surface depletion layer detectors have very low sensitivity to HFC's. One way to increase their sensitivity to HFC's is to increase the sensor operating temperature. However, this has the adverse effects of significantly shortening the life of the sensor and greatly increasing its sensitivity to other gases, particularly to chlorinated and/or brominated gases. This extreme sensitivity to minor impurities in the background atmosphere makes existing sensors unsuitable for detecting HFC's.

A solid state sensor having the ability of detecting the presence of many undesirable gases and vapors within an atmosphere is disclosed by Loh in U.S. Pat. No. 3,751,968. A solid state element, which contains alkali metal ions which readily accept negative ions of the subject gases and vapors, is brought into reactive contact therewith. The element is specially prepared to create an outer layer along its boundaries that is depleted of ions. The conductivity of the heated element in an atmosphere free of the reactive gases and vapors is low. However, the presence of one or more of the reactive gases and vapors causes ions to flow across the depletion boundary and increases the conductivity of the element. Electrical circuit means are provided for detecting an increase in the conductivity of the element and generating a signal indicative of the presence of a reactive constituent in the test atmosphere.

The Loh type device has proven to be an extremely useful tool for sensing the presence or absence of a halogen gas within a specific atmosphere. Special applications include leak detection in refrigeration equipment and the presence of potentially dangerous gases within an operating room or the like.

However, many test atmospheres contain more than one constituent that can react with the sensing element and, as a result, unwanted interference signals are sometimes generated that make it difficult to discern the presence of a single gas or vapor of immediate interest. Water vapor, which is ordinarily present in air, has the ability to trigger the sensor and has proven to be troublesome when air sampling is required. Hydrocarbons and chlorine atom containing cleaning solvents such as trichloroethylene have proven to be troublesome background gases commonly found in industrial environments. Because most prior art sensors have low sensitivity to gases which do not contain chlorine or bromine atoms, such as HFC's or sulfur hexafluoride, it has been almost impossible to detect the presence of these gases, particularly when interfering gases are present. The device is conventionally operated within the range of between 700° C. and 850° C. Increasing the sensor operating temperature increases the signal due to gases such as HFC's or sulfur hexafluoride, but also amplifies the unwanted interference signals thus negating any potential benefit. Increased operating temperature also significantly reduces the useful lifetime of the sensor.

SUMMARY OF THE INVENTION

It is therefore an object of the present invention to provide an improved detector for halogen containing gases, particularly HFC's, which has a relatively long operating life and is not subject to rapid deterioration in use.

A still further object of the present invention is to provide an improved detector for halogen containing gases which is sensitive not only to bromine and chlorine containing gases (such as Halons, CFC's, and HCFC's) but also to gases not containing chlorine or bromine (such as HFC's and sulfur hexafluoride).

A further object of the present invention is to provide an improved detector for halogen containing gases which has enough selectivity to detect fluorine containing gases such as R-134a in the presence of low levels of chlorinated or brominated gas impurities.

Yet another object of the present invention is to provide a miniaturized solid state detector for halogen containing gases having enhanced sensitivity and capable of inexpensive mass production by automated techniques.

Additional objects and advantages of the invention will become apparent to those skilled in the art from the description presented herein when taken in connection with the accompanying drawings.

BRIEF DESCRIPTION OF DRAWINGS

The specific details of a preferred embodiment of the invention and their mode of functioning will be particularly pointed out in clear, concise and exact terms in conjuction with the following drawings wherein.

DETAILED DESCRIPTION OF THE INVENTION

Figures 1, 2:
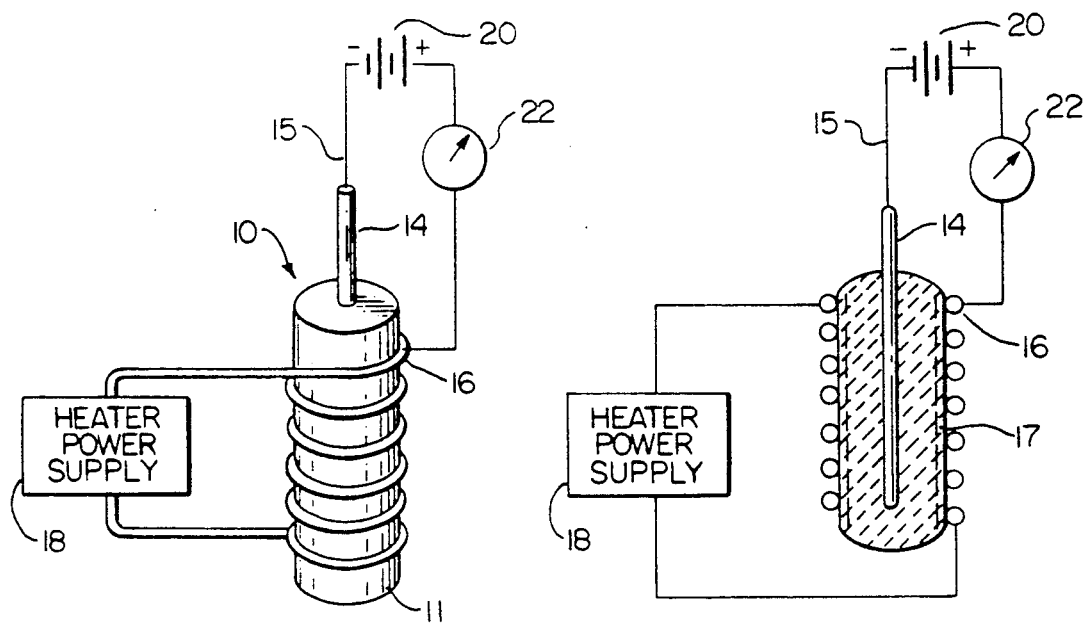
FIG. 1 is a perspective view of a sensor embodying the teachings of the invention shown connected in a schematically illustrated circuit.
FIG. 2 is an enlarged longitudinal cross-sectional view through the sensor as shown in FIG. 1.

Referring now more particularly to FIGS. 1 and 2 of the drawings, a sensor, shown generally at 10, is formed in a symmetrical configuration. This illustrated preferred embodiment is shown intended for the sensing of halogen containing gases, in which case the sensing element 11 is formed of a glass ceramic material. In the present invention, the ceramic is preferably composed of a mixture of an alkali metal silicate and oxides of aluminum and/or silicon, or it may be composed of aluminosilicate. The ceramic forms an electrically resistive layer between a cathode 14 and an anode 16. The electrodes can be platinum, palladium, alloys of platinum or palladium, or other metals which can survive the high operating temperature. The preferred ceramic composition is a mixture of potassium silicate, or sodium silicate, and silicon dioxide or aluminum oxide. The most preferred composition is a mixture of potassium silicate and aluminum oxide. A variety of weight ratios may be used. A weight ratio of one part aluminum oxide by weight to between about 0.25 and 4.0 parts potassium silicate by weight can be used in the practice of the invention. A preferred ratio is one part aluminum oxide by weight to between about 1.5 and 2.5 parts potassium silicate by weight. The composition of the potassium silicate is not critical and a weight ratio of one part potassium oxide to between about 1.6 and 2.5 parts silicon dioxide may be used. A particularly useful form of potassium silicate has been found to be KASIL ® (PQ Corporation, Valley Forge, Pa.) liquid potassium silicate. By way of example, KASIL ® 33 (PQ Corporation, Valley Forge, Pa.) is a water solution containing 36% by weight solids with a silicon dioxide to potassium oxide weight ratio of 2.1.

Aluminum oxide, silicon dioxide, and/or aluminosilicate can vary in particle size. The typical average particle size is less than 15 microns. A preferred average particle size is less than 1 micron.

The heater coil 16 also serves as an anode. It should be understood by those skilled in the art that a separate conductive element could serve as an anode without departing from the spirit of the invention.

The cathode typically is wire which varies from about 5 to 25 mil in diameter and about ¼ inch to 1 inch in length. The anode/heating element typically is a wire which varies from about 5 to 15 mil in diameter and about 2 inches to 5 inches in length. These dimensions are not critical and other wire sizes may be used.

In one embodiment of the invention, a sensor is made by coating a central platinum electrode with a slurry made from potassium silicate and aluminum oxide. Alternatively the slurry can be made from aluminosilicate. When the coating has dried, the coated wire is positioned inside the coils of a platinum wire anode formed into the shape of a cylindrical helix. Additional slurry is applied to fill any gaps between the anode coils and the first layer of slurry and the assembly is then fired. The preferred firing temperature is in the range of 600° C.-1,300° C. The firing step may be omitted. However, the length of the subsequent conditioning step necessary to form the depletion layer will be extended. The sensor element may be mounted in a suitable holder with electrically isolated leads allows electricity to flow to the sensor for activating the heater, applying a bias potential across the electrodes, and monitoring the current passing through the sensor. The sensor is conditioned by passing a current through the anode heater coil sufficient to produce a coil temperature of 600° C.-1,000° C. and simultaneously applying a DC voltage between one lead of the heater coil and the central electrode. A bias voltage of between 0.5 and 5 volts is applied such that the central electrode is held negative with respect to the heater coil. A depletion layer is formed in the ceramic by current passing between the electrodes. The current rapidly decreases during the first few hours of conditioning, but stabilizes within approximately 24 hours, indicating that the depletion layer has formed. Thereafter, in operation of the device, an ammeter 22, or similar device responsive to the flow of current between terminals 15 and 16 is arranged in the circuit. The ammeter 22 is illustratively shown in FIG. 1 as arranged in series with the sensor 10 and the biasing voltage power supply 20. If a halogen containing gas is present in the atmosphere adjacent sensor 10, the current passing through the sensing element increases and the increase is indicated by a change in the meter reading.

Sensors made from these materials can operate at temperatures between 800° C. and 1,100° C. for relatively long periods of time. At these temperatures, the ratio of response to CFC's (such as R-12) to response to HFC's (such as R-134a) is low enough that HFC's can be detected in the presence of low background levels of CFC's. These sensors can therefore serve the dual purpose of detecting HFC's as well as CFC's, HCFC's, and Halons.

Figures 3, 4:
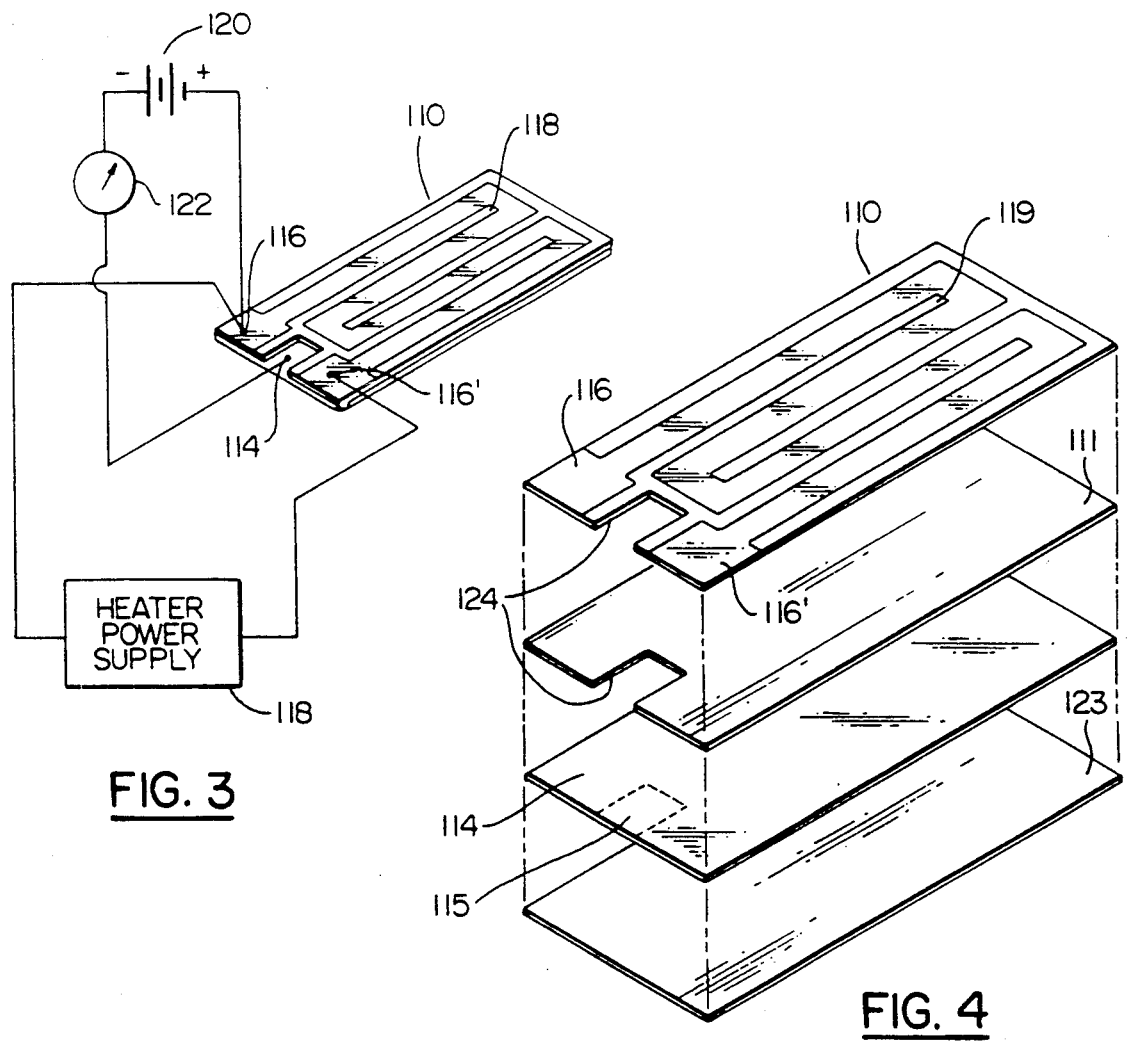
FIG. 3 is a perspective view of another embodiment showing another embodiment of a sensor constructed by microelectronic techniques that embodies the teachings of the present invention.
FIG. 4 is an exploded perspective view showing the component parts of the sensor illustrated in FIG. 3.

In another embodiment of the invention, the sensor may be in the form of a small planar structure, inexpensively fabricated in large quantities by techniques known to the microelectronics industry. Referring now to FIGS. 3 and 4 of the drawings, analogous components depicted in FIGS. 1 and 2 have the same numbers advanced by 100. The heating element 116 is a thin metallic film laid down on the ceramic 111 as a serpentine winding delineating intervening spaces 119 where the underlying ceramic 111 is exposed. The ceramic 111 is provided as a planar layer forming a barrier between the heating element and the cathode 114 which is a planar metallic film. A layer of ceramic substrate 123 underlies the cathode, functioning as a support for the assembly. Suitable slots 124 are provided in the ceramic and heating element layers for access to electrical contact point 115 at the cathode.

The sensor is conditioned as described above by forming the necessary depletion layer on an adjacent surface of the ceramic 111 by connecting cathode terminals 115 and heating element 116 across a biasing DC voltage of 0.5-5.0 volts, the cathode being negative with respect to the heating elements, and by connecting heating element terminals 116 and 116' to a heater power supply to produce a coil temperature in excess of 500° C. Thereafter, in operation of the device, an ammeter 122, or similar device responsive to the flow of current between terminals 115 and 116 is arranged in the circuit. The ammeter 122 is illustratively shown in FIG. 3 as arranged in series with the sensor 110 and the biasing voltage power supply 120. If a halogen containing gas is present in the atmosphere adjacent sensor 110, the current passing through the sensing element increases as will be immediately indicated on the ammeter.

Referring again to FIGS. 3 and 4 of the drawings, the planar sensor may be constructed by screen-printing a first conductive electrode layer 114 onto a ceramic substrate 123 using a platinum thick-film ink. After drying and firing this layer, the ceramic dielectric layer 111 is screen-printed over it in a pattern which provides notch 124 for access to electrical contact 115 for the buried electrode 114. This last layer is dried and cured. Thereafter, a second electrode/heater pattern 116 is screen-printed on the surface using platinum thick film ink. The final layer is then dried and fired.

Many variations of the planar construction are possible. One of these variations is to separate the function of the heater from that of the electrodes. In such a structure, the second electrode and heater element patterns are implemented as separate layers. The heater may be on the opposite side of the ceramic substrate from the first electrode, buried within the ceramic substrate, or adjacent the ceramic substrate on the same side thereof as the first electrode and separated from the first electrode by an electrically insulating layer.

The method of application of the various layers is not limited to screen printing, but may include sputter deposition, vapor deposition, plasma spraying, spin coating, or any other suitable means.

While the invention has been described in the specification and illustrated in the drawings with reference to a preferred embodiment, it will be understood by those of skill in the art that various changes may be made and equivalents may be substituted for elements of the invention without departing from the scope of the claims.

What is claimed is:

1. A solid state electrochemical device for detecting the presence of a halogenated gas contained within an atmosphere, said device comprising:
   (a) anode means;
   (b) cathode means;
   (c) a ceramic, comprising a mixture of potassium silicate and a compound selected from the group of silicon dioxide and aluminum oxide, interposed between said anode means and said cathode means, said ceramic being selectively reactive with fluorine containing gas in the presence of chlorine or bromine containing gas when said device is operated at a temperature of at least about 800° C.;
   (d) heating means for raising the temperature of said ceramic to a desired level;
   (e) electrical circuit means, connected across said anode means and said cathode means for holding said cathode means negative with respect to said anode means;
   (f) electrical measurement means connected in said electrical circuit means for providing an indication when said ceramic reacts with a given gas;
   (g) electrical power means connected to said electrical heating element means.

2. The device of claim 1 wherein said cathode means comprises an electrically conductive wire between about 5 to 25 mil in diameter and between about ¼ to 1 inch in length and said anode means comprises an electrically conductive wire between about 5 to 15 mil in diameter and about 2 to 5 inches in length.

3. The device of claim 1 wherein said device is constructed in planar configuration whereby said heating means comprises a first conductive film disposed in convoluted serpentine fashion over one surface of said device, said cathode means comprises a second conductive film, and said anode means comprises a third conductive film separated from said cathode means by said ceramic.

4. The device of claim 3 wherein said first conductive film and said third conductive film comprise one conductive film disposed in serpentine fashion and separated from said cathode means by said ceramic.

5. A solid state electrochemical device for detecting the presence of a halogenated gas contained within an atmosphere, said device comprising:
   (a) anode means;
   (b) cathode means;
   (c) a ceramic, comprising a mixture of potassium silicate and aluminum oxide in a ratio of between about 0.25-4.0 parts potassium silicate by weight to 1 part aluminum oxide by weight, interposed between said anode means and said cathode means, said ceramic being selectively reactive with fluorine containing gas in the presence of chlorine or bromine containing gas when said device is operated at a temperature of at least about 800° C.;
   (d) heating means for raising the temperature of said ceramic to a desired level;
   (e) electrical circuit means, connected across said anode means and said cathode means for holding said cathode means negative with respect to said anode means;
   (f) electrical measurement means connected in said electrical circuit means for providing an indication when said ceramic reacts with a given gas;
   (g) electrical power means connected to said electrical heating element means.

6. The device of claim 5 wherein said cathode means comprises an electrically conductive wire between about 5 to 25 mil in diameter and between about ¼ to 1 inch in length and said anode means comprises an electrically conductive wire between about 5 to 15 mil in diameter and about 2 to 5 inches in length.

7. The device of claim 5 wherein said device is constructed in planar configuration whereby said heating means comprises a first conductive film disposed in convoluted serpentine fashion over one surface of said device, said cathode means comprises a second conductive film, and said anode means comprises a third conductive film separated from said cathode means by said ceramic.

8. The device of claim 7 wherein said first conductive film and said third conductive film comprise one conductive film disposed in serpentine fashion and separated from said cathode means by said ceramic.

9. A solid state electrochemical device for detecting the presence of a halogenated gas contained within an atmosphere, said device comprising:
   (a) anode means;
   (b) cathode means;
   (c) a ceramic, comprising a mixture of potassium silicate and aluminum oxide in ratio of between about 1.5–2.5 parts potassium silicate by weight to 1 part aluminum oxide by weight, interposed between said anode means and said cathode means, said ceramic being selectively reactive with fluorine containing gas in the presence of chlorine or bromine containing gas when said device is operated at a temperature of at least about 800° C.;
   (d) heating means for raising the temperature of said ceramic to a desired level;
   (e) electrical circuit means, connected across said anode means and said cathode means for holding said cathode means negative with respect to said anode means;
   (f) electrical measurement means connected in said electrical circuit means for providing an indication when said ceramic reacts with a given gas;
   (g) electrical power means connected to said electrical heating element means.

10. The device of claim 9 wherein said cathode means comprises an electrically conductive wire between about 5 to 25 mil in diameter and between about ¼ to 1 inch in length and said anode means comprises an electrically conductive wire between about 5 to 15 mil in diameter and about 2 to 5 inches in length.

11. The device of claim 9 wherein said device is constructed in planar configuration whereby said heating means comprises a first conductive film disposed in convoluted serpentine fashion over one surface of said device, said cathode means comprises a second conductive film, and said anode means comprises a third conductive film separated from said cathode means by said ceramic.

12. The device of claim 11 wherein said first conductive film and said third conductive film comprise one conductive film disposed in serpentine fashion and separated from said cathode means by said ceramic.

* * * * *